(12) United States Patent
Mace

(10) Patent No.: US 8,922,920 B2
(45) Date of Patent: Dec. 30, 2014

(54) SELF-POSITIONING LIGHT FILTERING DEVICE AND REPLACEABLE FILTER

(71) Applicant: James Gordon Mace, Washington, MO (US)

(72) Inventor: James Gordon Mace, Washington, MO (US)

( * ) Notice: Subject to any disclaimer, the term of this patent is extended or adjusted under 35 U.S.C. 154(b) by 0 days.

(21) Appl. No.: 14/199,455

(22) Filed: Mar. 6, 2014

(65) Prior Publication Data

US 2014/0268385 A1     Sep. 18, 2014

Related U.S. Application Data

(60) Provisional application No. 61/776,913, filed on Mar. 12, 2013.

(51) Int. Cl.
| | |
|---|---|
| *G02B 5/22* | (2006.01) |
| *A61C 1/00* | (2006.01) |
| *G02B 7/00* | (2006.01) |
| *A61C 19/00* | (2006.01) |
| *A61F 9/02* | (2006.01) |

(52) U.S. Cl.
CPC ............... *G02B 7/006* (2013.01); *A61C 19/00* (2013.01); *A61F 9/02* (2013.01); *G02B 5/22* (2013.01)
USPC .............................................. 359/892; 433/29

(58) Field of Classification Search
None
See application file for complete search history.

(56) References Cited

U.S. PATENT DOCUMENTS

| | | | |
|---|---|---|---|
| 1,178,420 A | 4/1916 | Sibley | |
| 2,054,230 A | 9/1936 | Patterson | |
| 3,154,253 A | 10/1964 | Guth | |
| 4,214,393 A | 7/1980 | Long | |
| 4,392,188 A | 7/1983 | Norris | |
| 4,878,156 A | 10/1989 | Hallings et al. | |
| 5,288,231 A | 2/1994 | Kuehn et al. | |
| 5,537,205 A | 7/1996 | Costa et al. | |
| 5,749,724 A | 5/1998 | Cheng | |
| 5,759,032 A | 6/1998 | Bartel | |
| 6,011,219 A | 1/2000 | Casmero | |
| 6,155,823 A * | 12/2000 | Nagel | 433/29 |
| 6,325,623 B1 | 12/2001 | Melnyk et al. | |
| 6,345,982 B1 | 2/2002 | Meyer | |
| 6,384,420 B1 | 5/2002 | Doriguzzi Bozzo | |
| 7,658,013 B2 | 2/2010 | Tung | |
| 8,337,201 B1 | 12/2012 | Mace | |
| 2003/0008260 A1 | 1/2003 | Wang et al. | |
| 2004/0029069 A1 | 2/2004 | Gill et al. | |

(Continued)

FOREIGN PATENT DOCUMENTS

WO     2008120002 A1    10/2008

OTHER PUBLICATIONS

Henry Schein Dental 2012 Merchandise Catalog, pp. 347, 348, 349, 350, 353 and 354.

*Primary Examiner* — Jade R Chwasz
(74) *Attorney, Agent, or Firm* — Senniger Powers LLP

(57) ABSTRACT

A self-positioning light filtering device including a rotational bearing having concentric outer and inner components rotatable relative to one another. The inner component defines an opening for receiving the tip or other component of a light-emitting device. A transparent filter member filters optically harmful light emitted from the light-emitting device. The filter member and the inner component of the rotational bearing are rotatable relative to one another. A counterweight below the rotational bearing causes the filter member to remain in an upright position when the inner component of the rotational bearing rotates relative to the outer component. A replaceable filter member for the filtering device is also disclosed.

13 Claims, 10 Drawing Sheets

(56) References Cited

U.S. PATENT DOCUMENTS

| | | |
|---|---|---|
| 2006/0252005 A1 | 11/2006 | Feinbloom et al. |
| 2007/0134616 A1 | 6/2007 | Gill et al. |
| 2009/0176186 A1 | 7/2009 | Swift |
| 2010/0273123 A1 | 10/2010 | Mecher |
| 2011/0185465 A1 | 8/2011 | Prinkey |
| 2011/0236851 A1 | 9/2011 | Müller et al. |
| 2011/0240543 A1 | 10/2011 | Kozey |
| 2012/0070798 A1 | 3/2012 | Teitelbaum |

* cited by examiner

SELF-POSITIONING LIGHT FILTERING DEVICE AND REPLACEABLE FILTER

CROSS-REFERENCE TO RELATED APPLICATION

This application claims priority to U.S. Provisional Application Ser. No. 61/776,913, filed Mar. 12, 2013, the entirety of which is hereby incorporated by reference in its entirety.

FIELD OF THE INVENTION

The present invention generally relates to light filtering equipment, and more particularly to equipment used for eye protection.

BACKGROUND OF THE INVENTION

Various implements have been employed in dentistry to shield the eyes of the dentist and other care providers from the optically harmful light emitted from dental curing devices. The most commonly used implements are described below.

One implement comprises a handheld filtering member that is held over the patient's mouth while the composite is cured. This is disadvantageous in several ways. First, the time taken to reach for the filtering member and hold it in place compromises efficiency since the dental assistant could be performing other duties while the dentist is curing. Also, the filtering member can sometimes be forgotten and not used, leaving the care provider's eyes vulnerable to the optically harmful light. Furthermore, the filtering members are typically large and cumbersome to store and use.

Another implement comprises a cone that is placed over the tip of the curing device. However, the cone can interfere with placement of the tip in the correct position, can push matrix systems (which are sometimes precariously placed) out of their correct positions, and allows the optically harmful light to leak out of the perimeter of the cone.

Still another implement comprises a light filtering disc that fits over the tip of the dental cure light, rests near the base of the tip by the light itself, and is secured to the tip by a grommet or some other retentive feature. This filtering disc stays outside of the patient's mouth. The disadvantage of this type of tool is that it continually needs to be adjusted to get it into the right position as the curing light is maneuvered around the mouth. This requires an extra step for the operator or the operator is forced to lean into a field of view that allows him/her to see through the filtering disc. Furthermore, when attempting to cure teeth in the very back of the mouth, this type of filtering disc can interfere with tip placement by pressing against the face of the patient and need to be adjusted to allow proper tip placement.

In summary, all of these implements have drawbacks and are difficult to use. Some clinicians choose simply not to use a filtering device because no great options are on the market. The care providers are therefore at risk from the optically harmful light. Most of these clinicians attempt to place the tip in position and look away from the light while curing. This leads to inaccuracies in tip placement which sometimes require another cure in the correct position and/or short exposures to harmful light if the curing begins prior to looking away. Thus an opportunity and need exists in the marketplace for an improved design that overcomes many of the shortfalls of the aforementioned devices and affords dental care providers with an enhanced level of convenience and protection when using dental curing lights.

One such improved design is described in my U.S. Pat. No. 8,337,201 disclosing an improved self-positioning dental light filtering device.

SUMMARY

This invention is directed to a self-positioning light filtering device. In one embodiment, the light filtering device comprises a rotational bearing having concentric outer and inner components rotatable relative to one another about an axis of rotation. The inner component defines an opening for receiving the tip or other component of a light-emitting device (e.g., a dental curing light). The light filtering device also includes a transparent filter member for filtering optically harmful light emitted from the light-emitting device. The filter member and the inner component of the rotational bearing are rotatable relative to one another about the stated axis of rotation. A counterweight below the rotational bearing causes the filter member to remain in an upright position when the inner component of the rotational bearing rotates relative to the outer component, as when the tip of the light-emitting device and/or the light-emitting device itself is rotated about said axis of rotation.

In another aspect, this invention is directed to a replaceable filter for a light filtering device such as the device described in the preceding paragraph. The replaceable filter comprises a transparent filter member for filtering optically harmful light emitted from a light-emitting device. The replaceable filter is configured for releasable attachment to the light filtering device.

In still another aspect, this invention is directed to a replaceable curing light filter comprising a filter member having a first surface with a shape, a support having a second surface with a shape corresponding to the shape of the first surface, and an interference fit between the first and second surfaces forming a releasable attachment between the filter member and the support.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
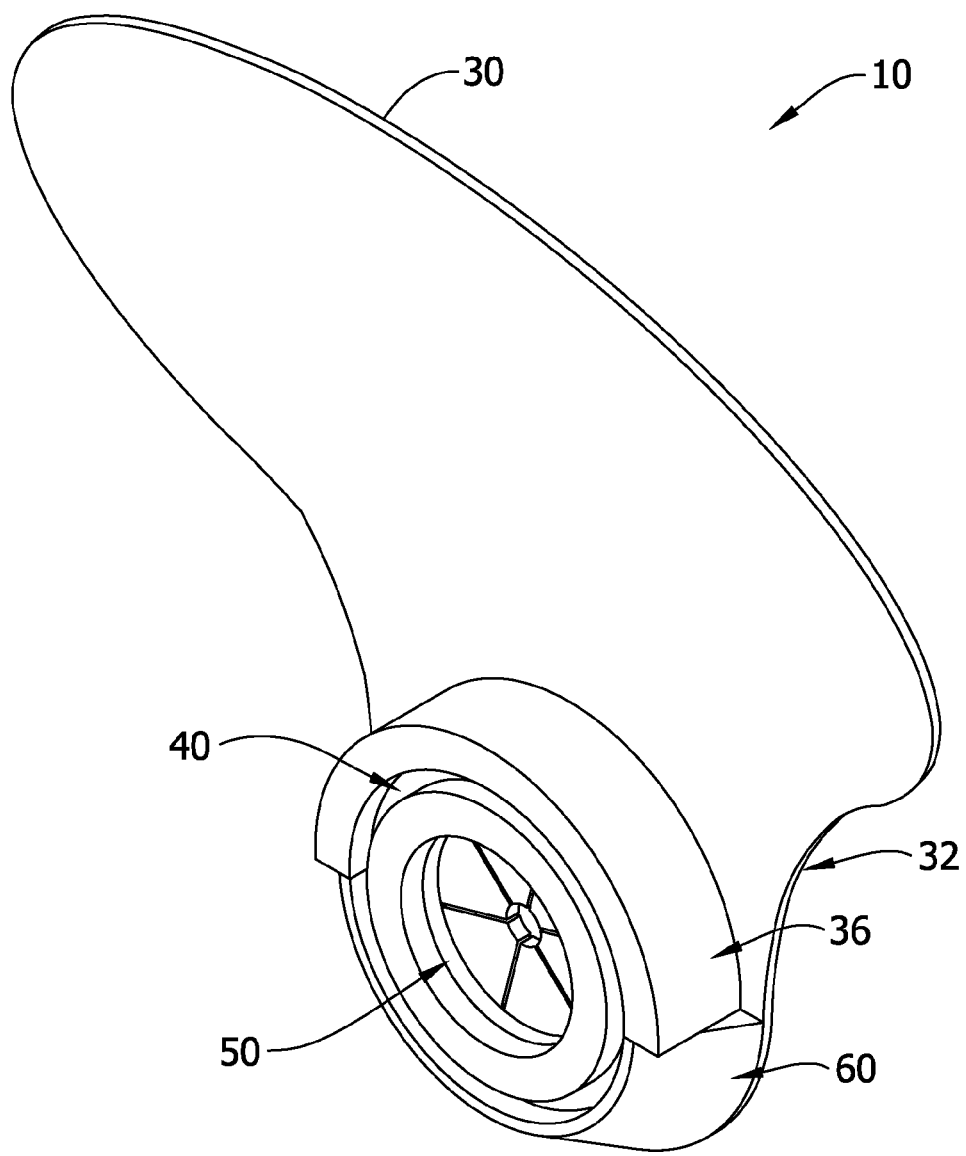
FIG. 1 is a perspective of a self-positioning dental light filtering device.

Referring now to the drawings, FIGS. 1-5 illustrate a self-positioning dental light filtering device, generally designated 10, as described in my U.S. Pat. No. 8,337,201, which is incorporated herein by reference. The light filtering device 10 is configured to be mounted on the tip or other component of a light-emitting device (e.g., a dental curing device) for blocking optically harmful light emitted from the device. A conventional dental curing device, generally designated 20, is depicted in phantom lines in FIG. 2. The curing device has a body 22 formed as a handle to be gripped by the care provider (e.g., dentist), and an elongate tip 24 extending forward from the body. The body 22 is equipped with a light-emitting device 26, such as an LED, that emits a curing light 28 through the tip 24, as will be understood by those skilled in the field of dentistry. Typically, the tip 24 can be rotated (manually) relative to the body 22 of the curing device 20 about the longitudinal axis 29 of the tip. The curing device 20 forms no part of this invention and will not be described in further detail.

The light filtering device 10 comprises a transparent filter member 30 of a color, tint or material for blocking optically harmful light 28 emitted from the tip 24 of the curing device 20, and a filter member support, generally designated 32, for supporting the filter member in an upright position above the tip 24 of the curing device 20. The light filtering device 10 also comprises a bearing mount, generally designated 36, affixed to the filter member support 32. The bearing mount 36 mounts a rotational bearing, generally designated 40, having concentric outer and inner components 42, 44 (FIG. 4), which are rotatable relative to one another about an axis of rotation 46. The outer component 42 is immovably affixed to the bearing mount 36. The inner component 44 defines an opening 38 (FIG. 5) concentric with the axis of rotation 46 for receiving the tip 24 of the curing device 20. A retaining device, generally designated 50, is provided in the opening 38 for holding the tip 24 of the curing device 20 substantially centered with the rotational bearing 40 (i.e., concentric with the axis of rotation 46 and also concentric with the longitudinal axis 29 of the tip) and substantially rotationally stationary relative to the inner component 44 of the rotational bearing 40 when the tip is received in the opening 38. A counterweight, generally designated 60, located below the rotational bearing 40 causes the filter member 30 to remain in its upright position when the tip 24 of the curing device 20 or the curing device 20 is rotated (by the care provider) about the axis of rotation 29. The components of the light filtering device 10 are described in more detail below.

The filter member 30 illustrated in the drawings is generally oval in shape, but it may have other shapes (e.g., circular, rectangular, polygonal) without departing from the scope of this invention. The filter member is of a material suitable for blocking harmful curing light 28 emitted by the curing device 20, which curing light typically is a blue light having a wavelength in the range of 450-500 nm. By way of example but not limitation, the filter member 30 may be of cell-cast acrylic. This type of acrylic is resistant to chemicals and has the desirable property of being transparent to allow optical clarity. One suitable color, amber 2422, is commonly available in the industry and is suitable for filtering the curing light 28 so that it is safe for viewing.

The oval shape of the filter member 30 allows for a small connection to the bearing and a larger viewing section in the superior position for eye protection. Desirably, the filter member 30 is of relatively thin sheet material (e.g., 1/32 in. sheet material, referred to the industry as 0.030 in. sheet). The relatively thin material is desirable to minimize the weight of the filter member 30 and offsetting counterweight 60.

Figure 4:
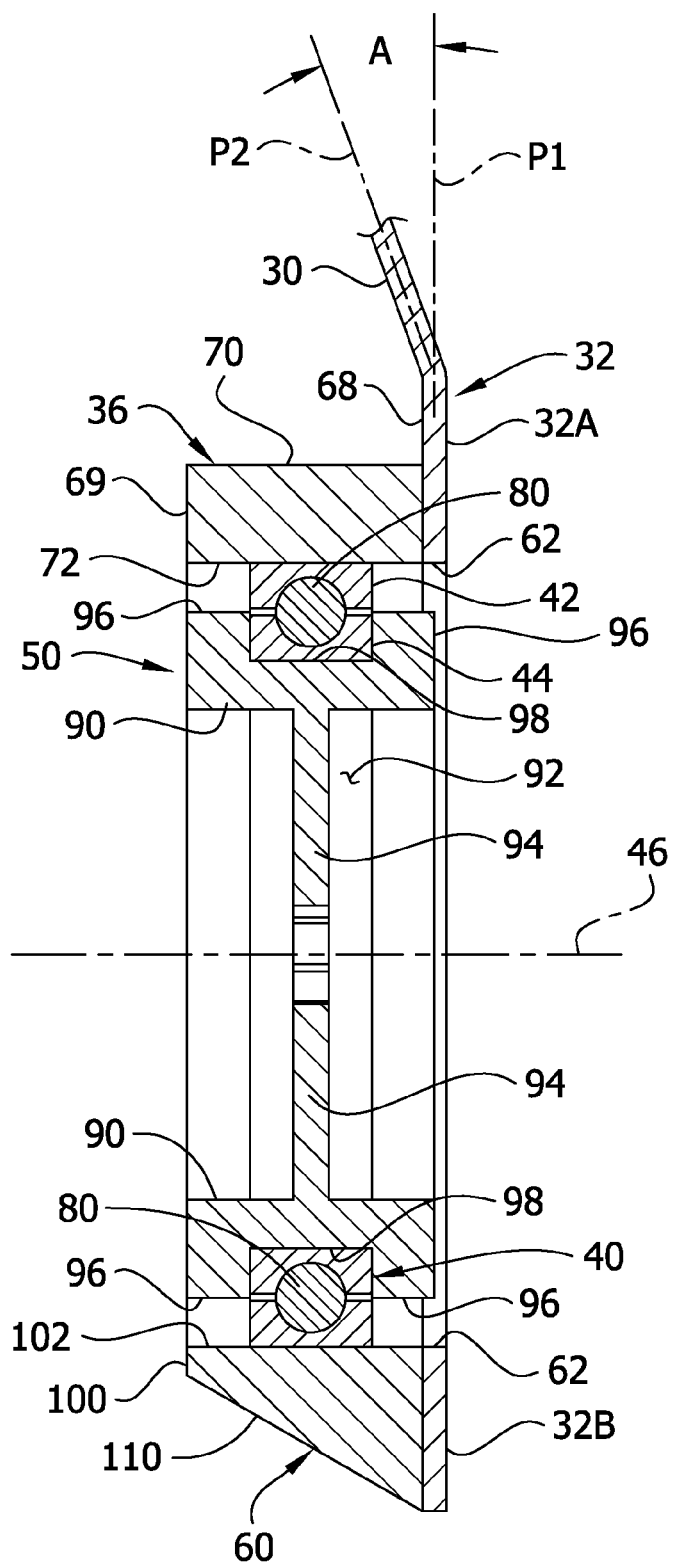
FIG. 4 is an enlarged vertical section taken in the plane of 4-4 of FIG. 3.

Referring to FIG. 4, the filter member support 32 has an upper generally planar section 32A disposed above the rotational bearing 40 and a lower generally co-planar section 32B disposed below the rotational bearing. The upper and lower sections 32A, 32B lie in a first plane P1 generally perpendicular to the axis of rotation 46 and define a circular opening 62 that is generally concentric with the opening 38 in the rotational bearing 40 and about the same size as that opening. The filter member 30 extends from the filter member support 32 and lies in a second plane P2 oriented at an angle A relative to the first plane P1. Desirably, this angle A is in the range of plus or minus 0-60 degrees, and even more desirably in the range of plus or minus 0-20 degrees. In one embodiment, the filter member support 32 and filter member 30 are integrally formed as one piece from the same material (e.g., cell-cast acrylic), but they may be formed as separate pieces of the same or different material and then attached to one another.

The filter member support 32 and/or filter member 30 can have configurations other than those described above without departing from the scope of this invention.

Figure 5:
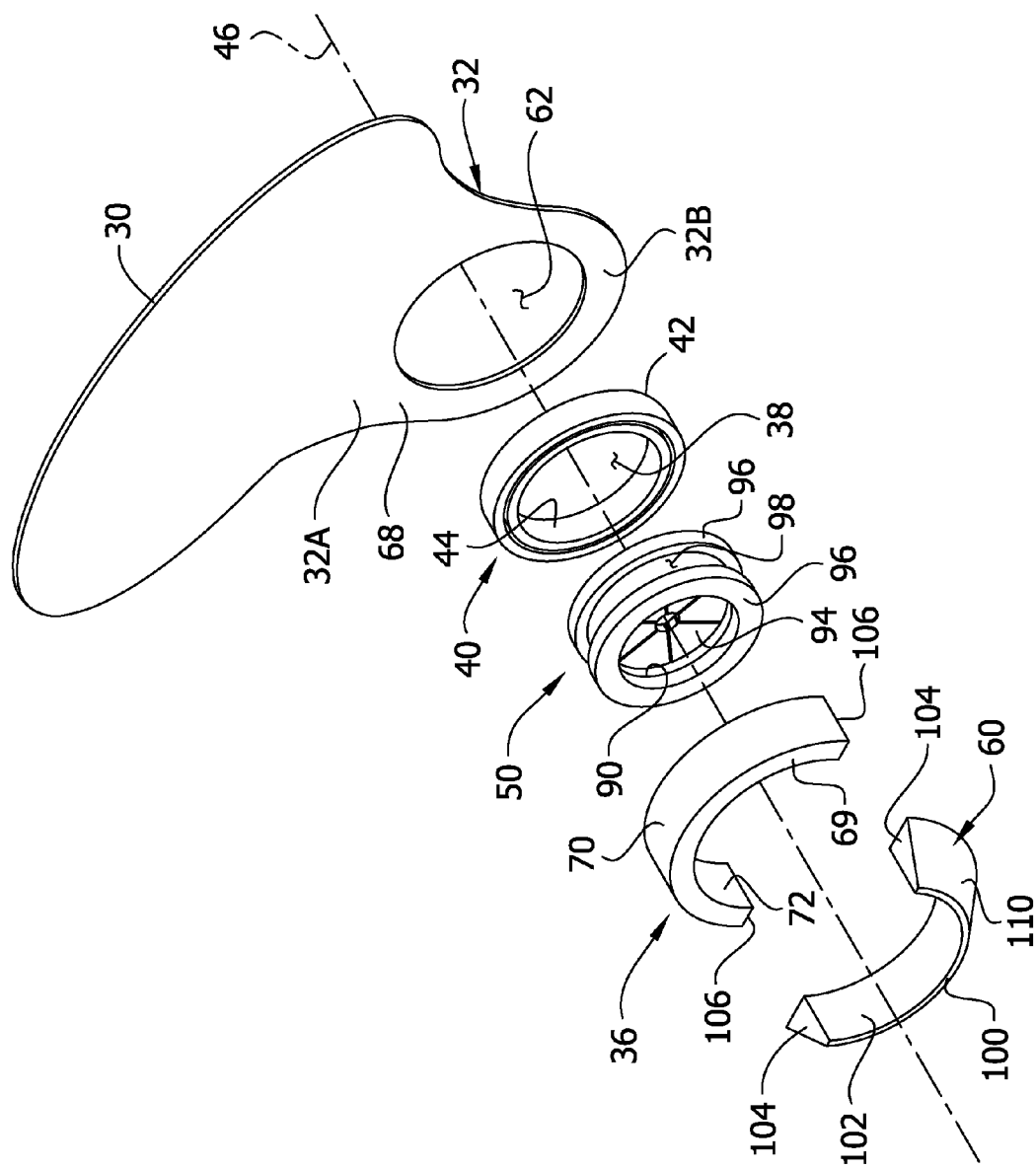
FIG. 5 is an exploded assembly view of the light filtering device showing various components.

Referring to FIGS. 4 and 5, the bearing mount 36 comprises a curved member 69 immovably affixed to one face 68 of the upper section 32A of the filter member support 32 and at least partially surrounding the outer component 42 of the rotational bearing. The curved member 69 has an upper surface 70 and a curved (e.g., semi-circular) lower surface 72 closely conforming to the curvature of the outer component 42 of the rotational bearing. At least the lower surface 72 and desirably both the upper and lower surfaces 70, 72 are generally concentric with the axis of rotation 46. By way of example, the curved member 69 may be a part-circular section (e.g., semi-circular section) of acrylic tubing adhered to the filter member support 32. The bearing mount 36 may have other configurations without departing from the scope of this invention.

In the illustrated embodiment, the rotational bearing 40 is a thin-section rolling-element bearing, such as a bearing commercially available from, for example, Alpine Bearing Co. in Allston, Mass. The outer component 42 of the bearing comprises an annular outer race, also designated 42, immovably affixed (e.g., adhered) to the curved lower surface 72 of the bearing mount 36 and to the counterweight 60. The inner component 44 of the bearing comprises an annular inner race, also designated 44, having an inside diameter defining the tip opening 38. Balls or other roller elements 80 positioned between the two races 42, 44 allow relative rotation between the inner and outer bearing components. The inside diameter (ID) of the inner annular race 44 is relatively close to the outside diameter (OD) of the outer annular race 42. By way of example, the difference between the ID and OD may be about 0.125 in. or less. A thin-section rotational bearing allows the bearing to be relatively small yet have a relatively large opening sufficient to accommodate the retaining device 50 and curing devices having tips of varying diameter. The bearing 40 is lubed with an oil of a viscosity that provides the right amount of movement without being too stiff. Other types of rotational bearings may also be used.

Figure 3:
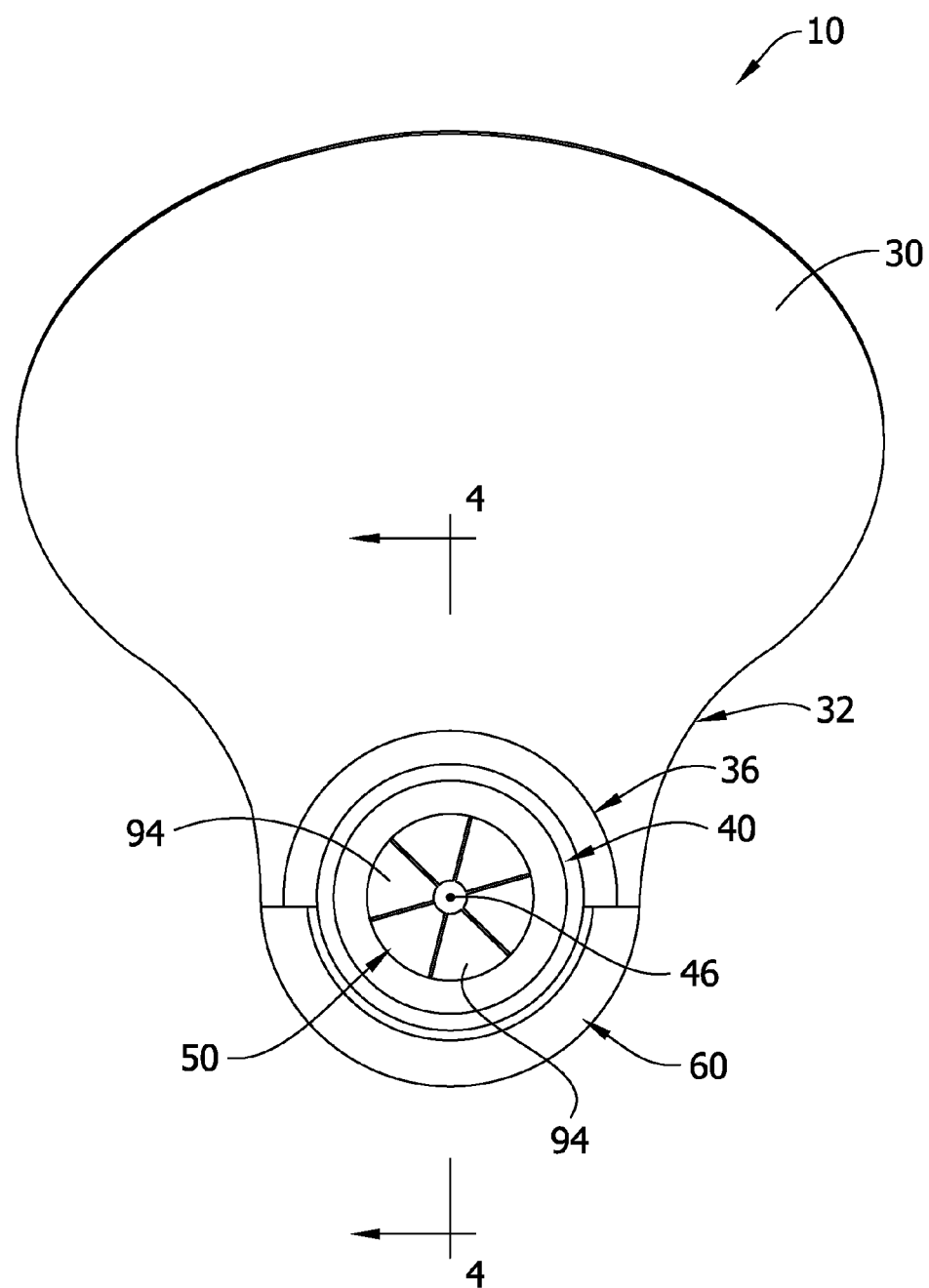
FIG. 3 is a front elevation of the light filtering device of FIG. 1.

Referring to FIGS. 3-5, the retaining device 50 comprises a ring 90 fitted inside the tip opening 38 defined by the inner component 44 of the rotational bearing. The ring 90 defines a central opening 92 concentric with axis 46 (see FIG. 4). Resilient tapered gripping members 94 extend inward into the opening 92 for gripping the tip 24 of the light-emitting device 20. The ring 90 includes a pair of annular flanges 96 projecting in a generally radial direction outward from the ring. The flanges 96 are spaced apart to define an annular groove 98 between the flanges for receiving the inner race 44 of the bearing 40. Desirably, the ring 90 and gripping members 94 are integrally formed (e.g., molded) as a one-piece structure of resilient material. The ring 90 is sized for a snap fit of the inner race 44 of the bearing 40 inside the groove 98. By way of example but not limitation, the ring 90 and gripping members 94 may be formed from 70-durometer rubber, which is rigid enough for securely holding the device 10 on the tip 24 of the curing device 20 but not so rigid that the tip cannot be easily snap-fit inside the rotational bearing 40. Further, the resilient nature of the retaining device 50 allows it to accommodate light tips 24 (or other curing device components) having substantially different diameters falling within a relatively wide range of sizes. The retaining device 50 may have other shapes without departing from the scope of this invention.

Referring to FIGS. 4 and 5, the counterweight 60 comprises a curved counterweight member 100 immovably affixed (e.g., adhered) to face 68 of the lower section 32B of the filter member support 32 and to the lower surface of the outer component 42 of the rotational bearing 40. The counterweight 60 is of a suitably heavy material, such as a tungsten alloy, a very dense yet non-toxic metal which minimizes the size of the counterweight. By way of example, the alloy may have a density in excess of 18 g/cm$^3$. Desirably, the counterweight member 100 has a curved generally part-circular upper surface 102 that wraps around and closely conforms in size and shape to the curved lower surface of the outer annular 44 race of the rotational bearing 40. (The outer race 44 is adhered to this surface 102.) The counterweight member 100 also has upward-facing end surfaces 104 that desirably seats against and are immovably affixed (e.g., adhered) to downward-facing end surfaces 106 of the bearing mount 36. The lower surface 110 of the counterweight member 100 tapers in a direction away from the filter member support 32 to facilitate partial entry into the mouth of a patient, as needed or desired.

The counterweight 60 may have other shapes and be placed at other locations on the filter member support 32 without departing from the scope of this invention. Further, while the illustrated counterweight comprises only one member, the counterweight can include two or more separate members.

The overall weight of the counterweight 60 is sufficient to offset the weight of the filter member 30 and maintain it upright as the tip 24 is turned and/or when the body 22 of the curing device 20 is rotated into position. By way of example, this weight may be in the range of 5-40 grams, and even more particularly in the range of 15-25 grams. Desirably, the counterweight 60 is positioned close enough to the rotational bearing 40 to prevent rocking as the filter member 30 approaches a resting position as determined by the counterweight. In the illustrated embodiment, the counterweight 60 is located immediately adjacent the rotational bearing 40, with the counterweight and rotational bearing spaced apart a distance no greater than 0-0.125 in. This location reduces the overall size of the light filtering device 10 for maximum compactness and also minimizes any pendulum-like rocking of the filter member 30 when the tip 24 or curing device 20 is rotated or repositioned by the care provider. However, the counterweight 60 can be located more remotely from the rotational bearing 40 without departing from the scope of this invention.

The components of the light filtering device 10 described above may be adhesively bonded together using a DP 190 epoxy available from 3M Company. It is clear for good esthetics, has a very high bond strength at room temperature, and is not brittle (making it flex slightly if the device is dropped to avoid breaking the adhesive bond).

Figure 2:
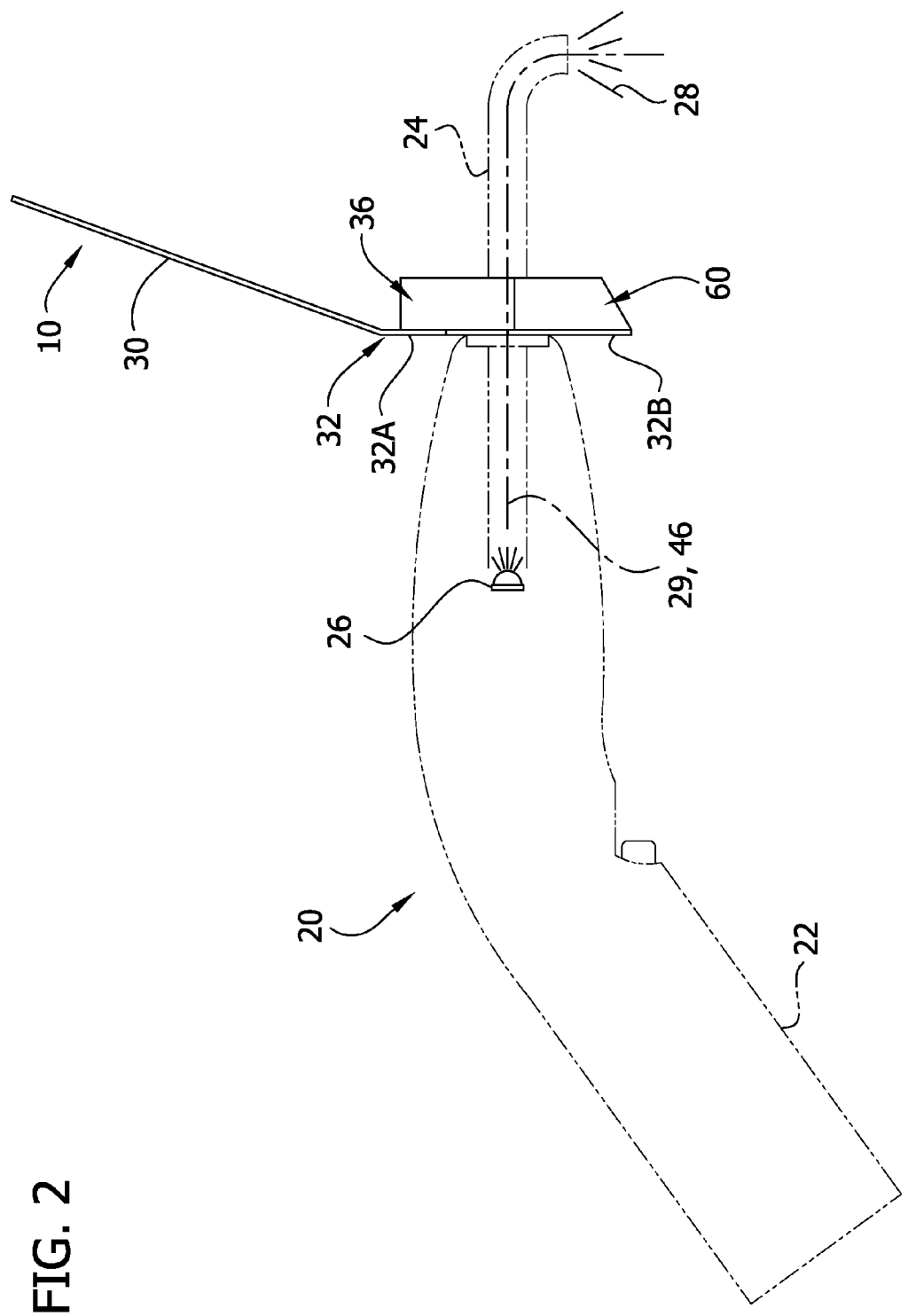
FIG. 2 is a side elevation of the light filtering device of FIG. 1 mounted on the tip of a dental curing device.

In use, the light filtering device 10 is installed on the tip 24 of the curing device, as illustrated in FIG. 2. As thus installed, the retaining device 50 grips the tip 24 and holds it substantially concentric with the axis of rotation 46 and rotationally stationary relative to the inner component 44 of the rotational bearing 40. Thus, when the care provider rotates the tip 24 of the curing device 20 and/or rotates or repositions the curing device itself during a procedure, the retaining device 50 and the inner component 44 of the rotational bearing 40 will rotate with the tip relative to the outer component 42 of the rotational bearing immovably affixed to the filter member support 32. The counterweight 60 functions to keep the filter member 30 upright and in proper position during the procedure to block curing light 28 emitted from the light-emitting device 26, regardless of how the tip 24 is turned, the patient is turned or tilted, or how the curing device is rotated. In effect, the light filtering device 10 "self-positions" during the procedure to remain in the proper upright orientation, without the need for any adjustment or repositioning by the care provider or other person.

It will be observed that the primary movement of the body 22 and tip 24 of the curing device 20 is rotational as the clinician determines the correct position. Sometimes during use the body 22 of the curing device 20 may be rotated one way and the tip 24 grasped and rotated in an opposite direction to reach the desired spot in a patient's mouth. Having a filter member 30 that maintains its upright position during these movements creates operational efficiency. In view of the rotational movements of the body and light tip of the curing device, the rotational bearing 40 positioned in the plane of these movements facilitates auto-positioning of the device. This arrangement also allows the light tip to protrude through the inside of the bearing.

As noted above, a light filtering device 10 of this invention permits operational efficiencies. By way of example, a clinician curing a composite resin does not need to hold the curing device 20 with one hand and rotate the filter member 30 with the other to achieve the correct position; one hand is adequate. Also, if the position of the filter member 30 needs to be rotated slightly, it is easily done with a nudge with either hand. The body 22 of the curing device 20 does not need to be grasped tightly to rotate the filter member 30. Still further, using the light filtering device 10, only one individual is needed to cure the composite.

The light-filtering device of my invention can be used to block optically harmful light emitted from light-emitting devices other than dental curing devices, such as welding devices and laser devices.

Figure 6:
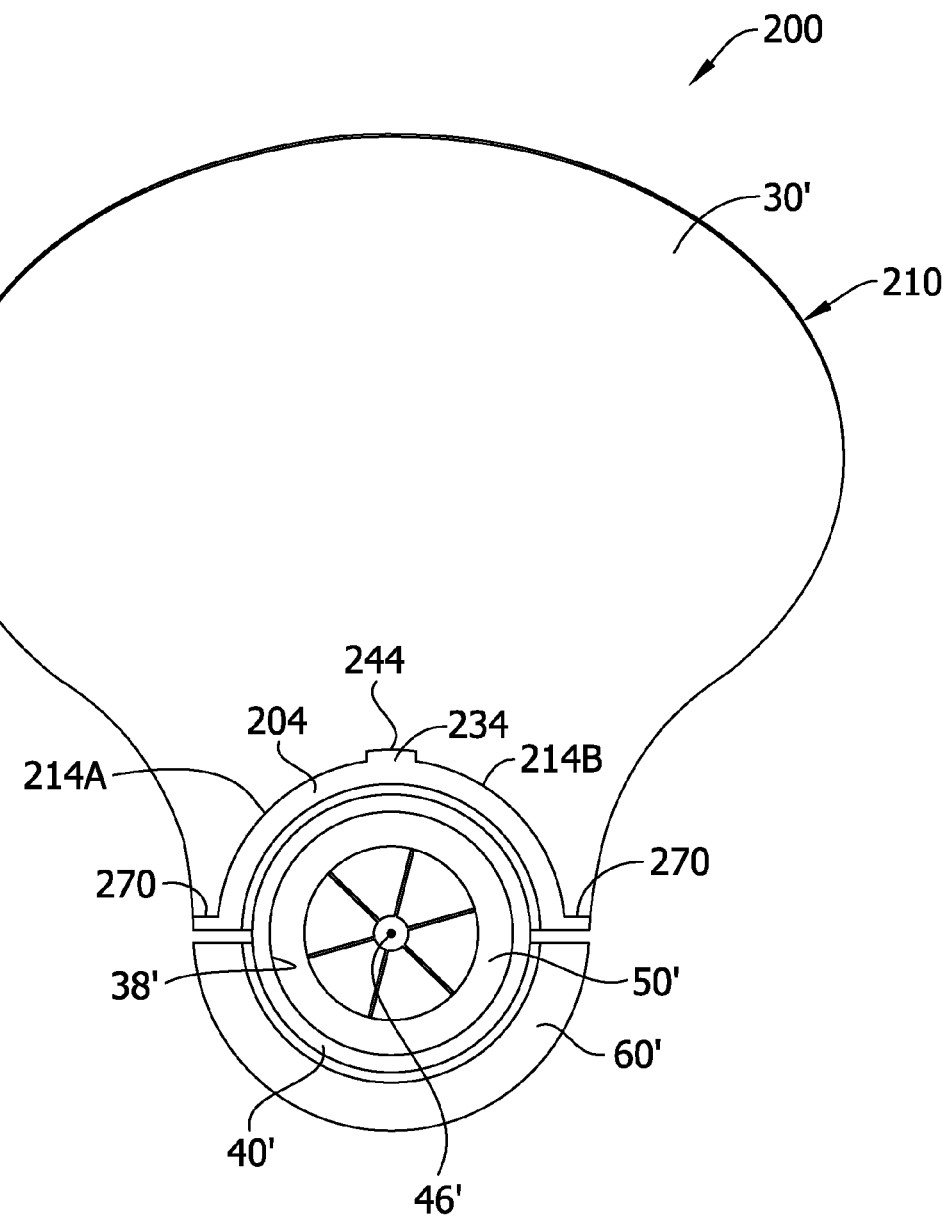
FIG. 6 is front elevation of a second embodiment of a self-positioning light filtering device comprising a replaceable filter member.
Figure 7:
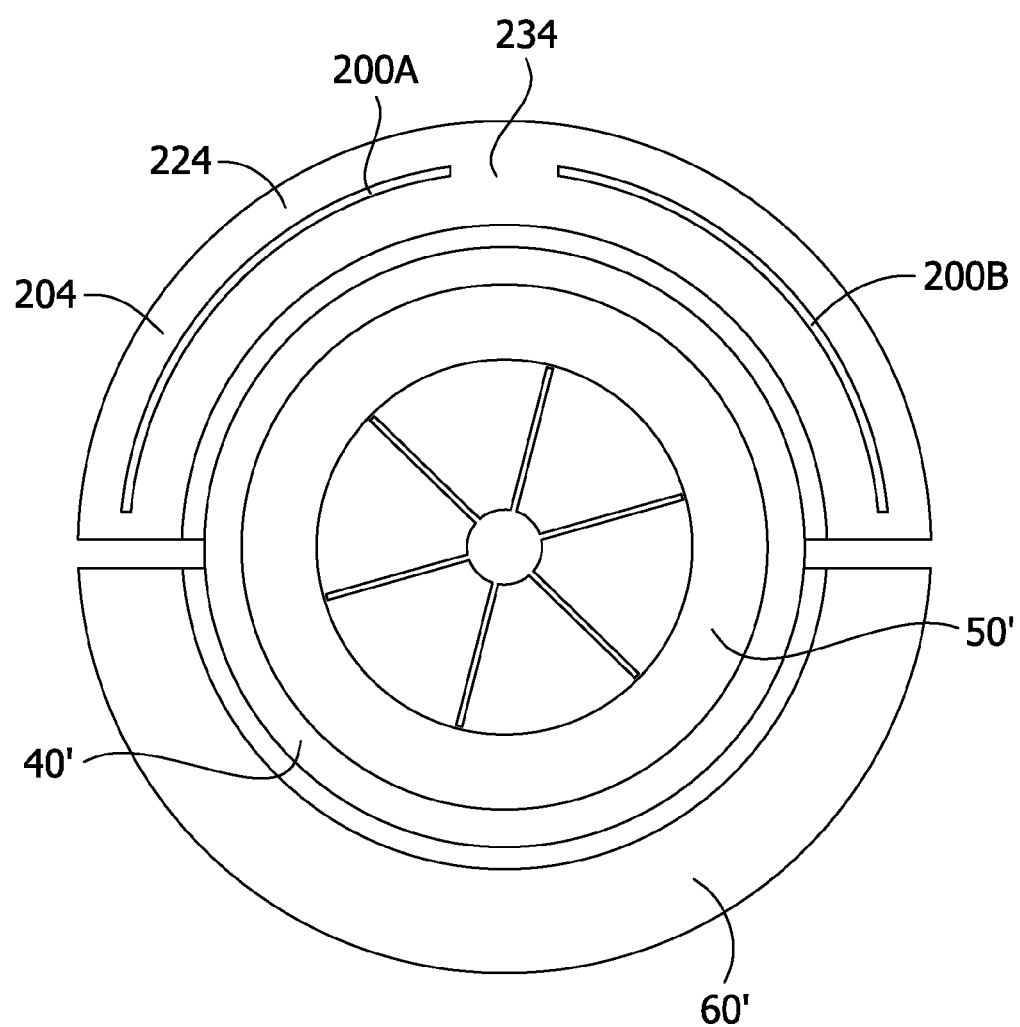
FIG. 7 is a front elevation of the light filtering device of FIG. 6 with the filter member removed.

FIG. 6 illustrates another embodiment of a light filtering device of this invention, generally designated 200. The light filtering device 200 is similar to the device 10 of the previous embodiment, and corresponding parts are designated by corresponding reference numbers with a prime (').

The light filtering device 200 comprises a rotational bearing, generally designated 40', having concentric outer and inner components which are rotatable relative to one another about an axis of rotation 46'. (The outer and inner components of the bearing 40' are not shown in FIG. 6, but they are identical to the outer and inner components 42, 44 of the previous embodiment.) The device 200 also includes a transparent filter member, generally designated 30', of a color, tint or material for blocking optically harmful light emitted from a light-emitting device, such as the dental curing device 20 previously described. The filter member 30' is configured for releasable attachment to a part-circular filter member support comprising a part-circular base 204 (comparable to the bearing mount 36 of the first embodiment) affixed to the outer component of the rotational bearing. The inner component of the bearing 40' defines an opening 38' concentric with the axis of rotation 46' for receiving the light emitting device. A retaining device, generally designated 50', is provided in the opening 38' for holding the light-emitting device substantially centered in the rotational bearing 40' (i.e., concentric with the axis of rotation 46') and substantially rotationally stationary relative to the inner component of the rotational bearing 40' when the light-emitting device is received in the opening 38'. A counterweight, generally designated 60', located below the rotational bearing 40' causes the filter member 30' to remain in its upright position when the light-emitting device is rotated (by the care provider or operator) about the axis of rotation 46'.

Figure 8:
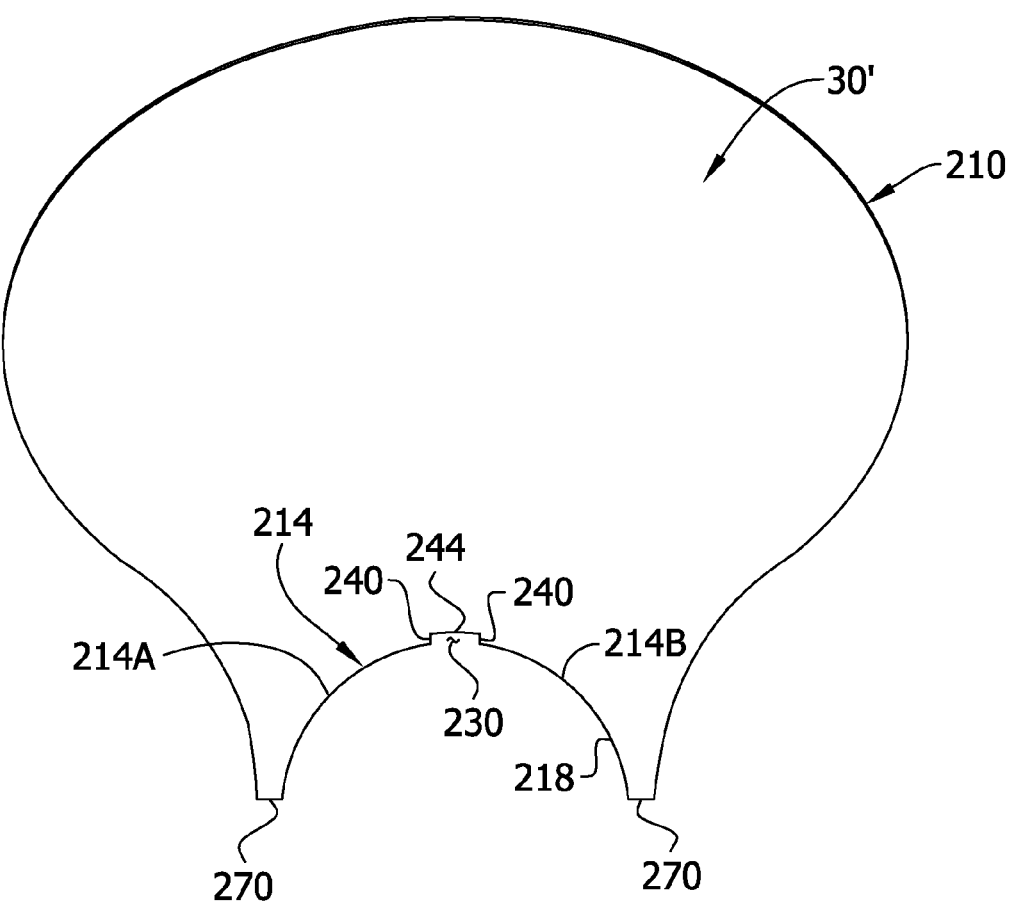
FIG. 8 is a front elevation of the removable filter member.
Figure 9:
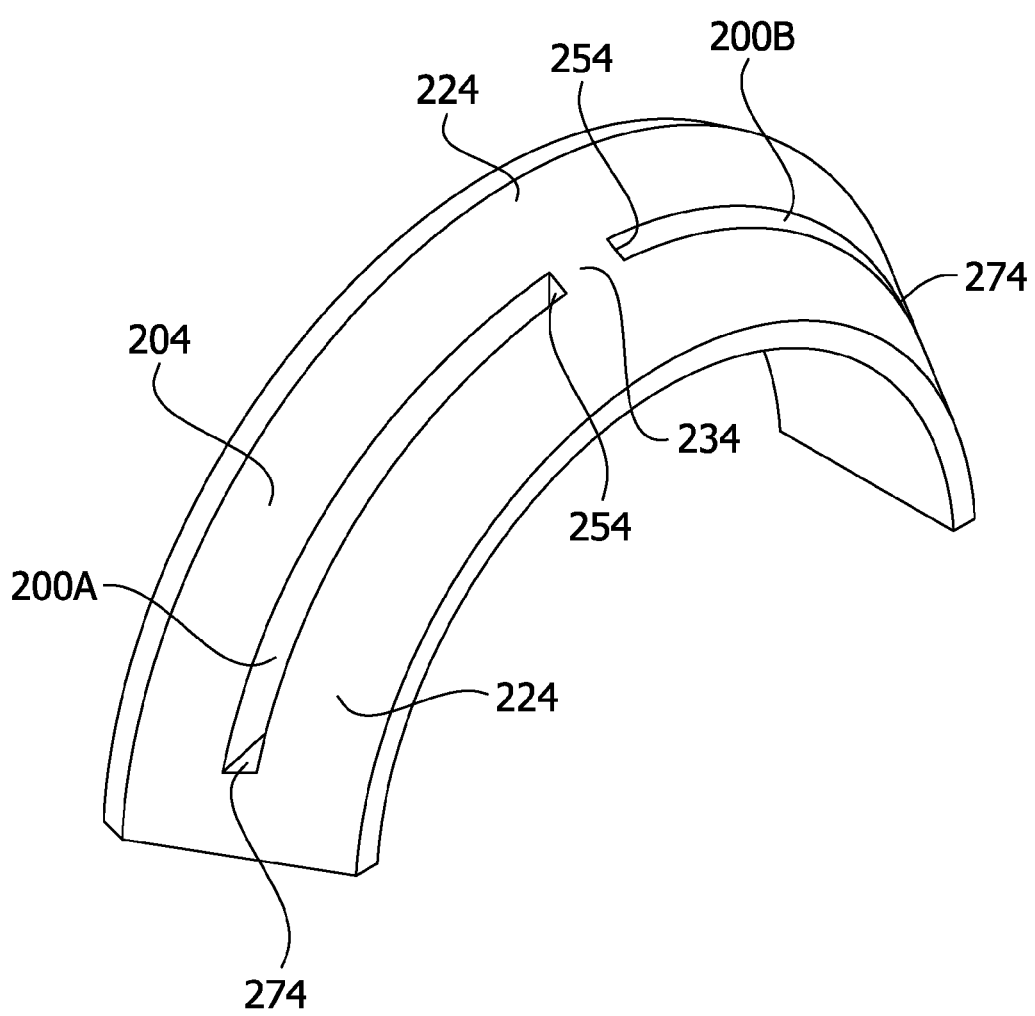
FIG. 9 is a perspective of a support for the filter member.

Referring to FIGS. 8 and 9, the filter member 30' has an outer periphery, generally designated 210, that includes a lower edge margin 214 terminating in a lower edge 218. In the illustrated embodiment, the lower edge 218 is generally semi-circular, but it may have other shapes. By way of example but not limitation, the lower edge may extend substantially more or less than 180 degrees. Further, the edge may be continuous or discontinuous (e.g., interrupted to form any number of extensions or tabs). The lower edge margin 214 is configured for releasable reception in one or more slots in the upper surface 224 of the base 204 of the light filtering device 200. In the illustrated embodiment, the lower edge margin 214 comprises a first edge margin segment 214A configured (e.g., as a curved extension or tab) for releasable reception in a first slot 200A, a second edge margin segment 214B configured (e.g., as a curved extension or tab) for releasable reception in a second slot 200B, and a notch 230 separating the first and second edge margin segments 214A, 214B for receiving a portion 234 of the base 204 located between the first and second slots 200A, 200B (see FIG. 9). The edge margin segments 214A, 214B are configured to have interference fits (i.e., press or friction fits) in respective slots 200A, 200B. In one embodiment, this is achieved by making the thickness of the filter member 30' at the lower edge margin segments 214A, 214B only slightly less than the widths of respective slots 200A, 200B. (Slot width is the dimension transverse to slot length.)

Referring to FIG. 8, the notch 230 in the filter member 30' is rectangular, having opposing generally vertical side edges 240 and a generally horizontal top edge 244. In other embodiments, the notch may have different shapes (e.g., rounded). Desirably, the top edge 244 of the notch has a contour that conforms to the contour of the upper surface 224 of the portion 234 of the base 204 located between the slots 200A, 200B. Further, the notch has a width (side-to-side dimension) only slightly greater than the spacing between the slots 200A, 200B. The arrangement is such that when the edge margins segments 214A, 214B of the filter member 30' are inserted into respective slots 200A, 200B to a depth sufficient to bring the top edge 244 of the notch 230 into contact with the portion 234 of the base 204, the side edges 240 of the notch have a relatively close fit with respective slot-end surfaces 254 extending generally vertically down from the portion 234 of the base (see FIG. 9). In addition, the filter member 30' has generally horizontal abutments 270 at opposite ends of its lower edge 218. When the edge margins segments 214A, 214B of the filter member 30' are inserted into respective slots 200A, 200B to a depth sufficient to bring the top edge 244 of the notch 230 into contact (or near contact) with the portion 234 of the base 204, the abutments 270 abut respective generally horizontal slot-end surfaces 274 extending from the upper surface 224 of the base 204 (see FIG. 9).

To install the replaceable filter 30', the edge margin segments 214A, 214B of the filter member 30' are inserted (press fit) into respective slots 200A, 200B until the top edge 244 of the notch 230 is in contact (or near contact) with portion 234 of the base 204 and the abutments 270 are in abutment (or near abutment) with respective slot-end surfaces 274. As thus installed, the filter member 30' is precisely located relative to the base 204 by the close fit of the portion 234 of the base 204 in the notch 244, and the filter member is securely, stably, and releasably held in position against movement relative to the base. When needed or desired, the filter member 30' is readily removable from the slots 200A, 200B for replacement by a different filter member.

It will be understood that the filter member 30' and base 204 may have other configurations. By way of example, the number, configuration, and arrangement of the slots 200 may vary. Further, multiple sets of slots may be provided and configured for releasable reception of different filter members having lower edge margins of different thicknesses. The lower edge margin 214 of the filter member 30' may also have other configurations. The filter member 210 and its lower edge margin 214 may be formed (e.g., molded) as an integral one-piece structure, or they may be fabricated as separate parts and/or of different materials and then secured together.

As noted above, the notch 244 in the filter member 30' functions as a positioning device for precisely positioning the filter member relative to the base 204. Other types of positioning devices may be used for precisely positioning the filter member on the light filtering device.

In certain embodiments, a replaceable light filter of this invention comprises a filter member (e.g., 30') having a first surface (e.g., edge margin 214) with a shape, and a filter member support (e.g., base 204) having a second surface (e.g., slot surfaces) with a shape corresponding to the shape of the first surface, and an interference fit between the first and second surfaces forming a releasable attachment between the filter member and the filter member support. In some embodiments, the first surface of the filter member comprises at least one extension (e.g., edge margin segments 214A, 214B) projecting from a periphery of the filter member, and the second surface of the filter member support has at least one opening (e.g., slots 200A, 200B) for receiving the at least one extension. The filter member and filter member support may also be configured (e.g., notch 230 and base portion 234) to have a fit that establishes a precise predetermined position of the filter member on the filter member support.

Figure 10:
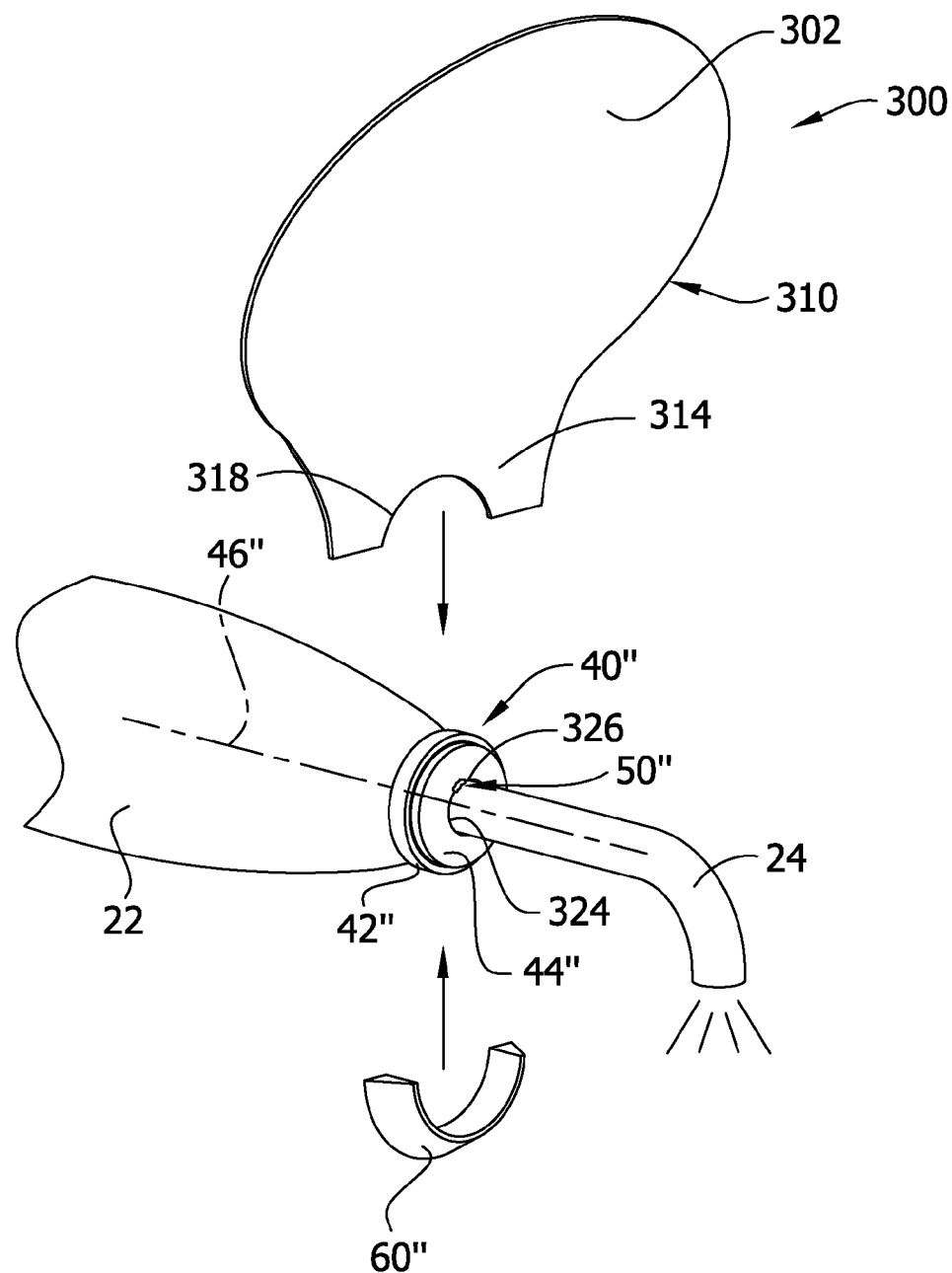
FIG. 10 is a perspective of a third embodiment of a self-positioning dental light filtering device of this invention.

FIG. 10 illustrates another embodiment of a light filtering device of this invention, generally designated 300, for blocking optically harmful light emitted by a light-emitting device, e.g., emitted from the tip 24 of a dental curing device 22. The light filtering device 200 is similar to the device 10 of the previous embodiment, and corresponding parts are designated by corresponding reference numbers with a double prime (''). The device 200 comprises a rotational bearing 40'' having concentric outer and inner components 42'', 44'' rotatable relative to one another about an axis of rotation 46''. A filter member 302 is attached to an upper surface of the outer component 42'' of the bearing for blocking optically harmful light. A counterweight 60'' is attached to a lower surface of the outer component 42'' of the bearing.

In this embodiment, the retaining device 50'' comprises an inner surface 324 of the inner bearing component 44'' configured for an interference friction fit with the tip 24 or other component of the light-emitting device 22 to hold the tip or other component substantially centered inside the rotational bearing and substantially rotationally stationary relative to the inner component of the rotational bearing when the tip or other component is received in the opening. Alternatively, or in addition, the retaining device 50'' comprises an adhesive 326 adhering the inner component of the rotational bearing to the tip 24 or other component of the light-emitting device 22 to hold the tip or other component substantially centered inside the rotational bearing and substantially rotationally stationary relative to the inner component of the rotational bearing when the tip or other component is received in the opening.

In the embodiment of FIG. 10, the filter member 302 has a non-releasable (permanent) attachment to the outer component 42" of the rotational bearing 40". In particular, the filter member 302 has an outer periphery 310 that includes a lower edge margin 314 terminating in a lower edge 318 having a contour or shape that approximates the contour or shape of the upper surface of the outer component 42" of the rotational bearing. The lower edge margin 314 is adhered directly to the upper surface of the outer bearing component 42" by adhesive or other suitable bonding agent. As thus adhered to the bearing component 42", the lower edge margin 314 acts as a filter member support for supporting the filter member 302 in an upright position. The counterweight 60" causes the filter member to remain upright when the tip of the curing device and/or the curing device itself is rotated about the axis 46".

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions without departing from the scope of the invention, it is intended that all matter contained in the above description and shown in the accompanying drawing[s] shall be interpreted as illustrative and not in a limiting sense.

What is claimed is:

1. A self-positioning light filtering device, comprising
a rotational bearing having concentric outer and inner components rotatable relative to one another about an axis of rotation, the inner component defining an opening for receiving the tip or other component of a dental curing device,
a transparent filter member for filtering said optically harmful light emitted from the dental curing device, said filter member and said inner component of the rotational bearing being rotatable relative to one another about said axis, and
a counterweight below the rotational bearing for causing the filter member to remain in an upright position when the inner component of the rotational bearing rotates relative to the outer component, as when the tip of the dental curing device and/or the dental curing device itself is rotated about said axis of rotation.

2. The light filtering device of claim 1, wherein the filter member is immovable relative to the outer component of the rotational bearing.

3. The light filtering device of claim 1, further comprising a filter member support for supporting the filter member in said upright position.

4. The light filtering device of claim 3, wherein the filter member support comprises a lower edge margin of the filter member having a shape approximating a shape of the outer component of the rotational bearing, and wherein said lower edge margin is adhered by adhesive to the outer component.

5. The light filtering device of claim 3, wherein said filter member support comprises a base attached to the outer component of the rotational bearing, and wherein the filter member is configured for releasable attachment to the base.

6. The light filtering device of claim 5, wherein said filter member has a lower edge margin terminating in a lower edge, said lower edge margin being configured for releasable reception in one or more slots in the base.

7. The light filtering device of claim 6, wherein the lower edge margin of the filter member is configured for an interference fit in said one or more slots.

8. The light filtering device of claim 7, wherein the lower edge margin of the filter member comprises a first edge margin segment configured for releasable reception in a first slot of said one or more slots, a second edge margin segment configured for releasable reception in a second slot of said one or more slots, and a notch separating the first and second edge margin segments for receiving a portion of the base between the first and second slots.

9. The light filtering device of claim 6, wherein said one or more slots include multiple slots in the base configured for releasable reception of different filter members having lower edge margins of different thicknesses.

10. The light filtering device of claim 3, wherein the filter member and filter member support are configured to have a fit that establishes a precise predetermined position of the filter member on the filter member support.

11. The light filtering device of claim 1, further comprising a retaining device for holding the tip or other component of the dental curing device substantially rotationally stationary relative to the inner component of the rotational bearing when the tip or other component is received in the opening.

12. The light filtering device of claim 11, wherein the retaining device comprises a surface of the inner bearing component configured for an interference friction fit with the tip or other component of the curing device to hold the tip or other component substantially centered inside the rotational bearing and substantially rotationally stationary relative to the inner component of the rotational bearing when the tip or other component is received in the opening.

13. The light filtering device of claim 11, wherein the retaining device comprises an adhesive adhering the inner component of the rotational bearing to the tip or other component of the dental curing device to hold the tip or other component substantially centered inside the rotational bearing and substantially rotationally stationary relative to the inner component of the rotational bearing when the tip or other component is received in the opening.

\* \* \* \* \*